United States Patent [19]

Cipriani et al.

[11] 4,307,256

[45] Dec. 22, 1981

[54] PROCESS FOR THE PREPARATION OF ALKYLENE GLYCOLS

[75] Inventors: Gioacchino Cipriani; Carlo Neri; Ugo Romano, all of S. Donato Milanese, Italy

[73] Assignee: Anic S.p.A., Palermo, Italy

[21] Appl. No.: 674,764

[22] Filed: Apr. 8, 1976

[30] Foreign Application Priority Data

Apr. 9, 1975 [IT] Italy ................................ 22145 A/75

[51] Int. Cl.³ ............................................ C07C 29/15
[52] U.S. Cl. ...................................... 568/867; 568/680
[58] Field of Search ...................... 260/635 E; 568/867

[56] References Cited

U.S. PATENT DOCUMENTS 3,629,343 12/1971 Levin et al. ...................... 260/635 E

OTHER PUBLICATIONS

Weber et al., Chem. Abst., 124008p, vol. 78 (1973), citing Ger. Offen. No. 2,141,470, 2/22/73.
Fumasoni et al., Chem. Abst., vol. 80, 14593j (1974), citing Ger. Offen. No. 2,318,327, 10/18/73.
Matin et al., Chem. Abst., vol. 77, 87370g (1972).

*Primary Examiner*—G. T. Breitenstein
*Attorney, Agent, or Firm*—Morgan, Finnegan, Pine, Foley & Lee

[57] ABSTRACT

A process for the preparation of alkylene glycols starting from the corresponding alkylene oxide, which is reacted with water in the presence of carbon dioxide, wherein the reaction catalyst is selected amongst the organic bases, preferably a tertiary amine, whereby the conversion rate and the selectivity are improved.

7 Claims, No Drawings

PROCESS FOR THE PREPARATION OF ALKYLENE GLYCOLS

The present invention relates to a process for the preparation of alkylene glycols, starting from the corresponding alkelene oxides, which are treated with water and carbon dioxide in the presence of a suitable catalytic system.

It is known that the production of glycols starting from olefinic oxides is normally carried out in liquid phase, in absence of catlysts and at 150° C., by using a water excess of about 10 to 15 moles with respect to one mole of the olefinic oxide.

It is alternatively possible to carry out the same reaction at lower temperature (80°–100° C.) in the presence of acidic or basic catalysts.

According to these processes, for a complete conversion of the oxide, a 20% water solution of the glycol is obtained, and di- and tri-glycols are formed in an amount of 13 to 16% by weight referred to the monoglycol.

Furtthermore, according to the U.K. Pat. No. 1,177,877, it is possible, in the presence of quarternary ammonium salts, to carry out the addition of $CO_2$, in the presence of water, to the alkylene oxides to obtain alkylene carbonates, which are then hydrolized to the glycols under high temperature and pressure.

It has now been found, which is the subject of the present invention, that alkylene glycols can be obtained starting from alkylene oxides with high selectivity rate and with an almost complete conversion of the oxide, by reacting the oxide with water, even in an almost stechiometrical amount, in the presence of carbon dioxide and of a catalyst consisting of an organic base.

To this end there are useful compounds having the formula

wherein $R_1$, $R_2$, $R_3$, which are alike or different from each other, represent alkyl, aryl or cycloalkyl groups, or even cycloaliphatic amines and heterocyclic nitrogen compounds of the class comprising pyridine, quinoline, diazine, triazine, imidazoles, oxazoles, and the like.

The concentration of the catalyst varies between 0.1% and 20% by weight referred to the feed; the $CO_2$ pressure varies between 1 and 50 kg./sq.cm., and the temperature between 50° and 150° C.

The operating details will be more evident from the following illustrative examples, which, however, should not be construed in limitative sense.

EXAMPLE 1

30.3 g. of ethylene oxide (ETO), 26.2 g. of water and 5.1 g. of triethylamine (TEA) were charged in a 250 ml autoclave, equipped with a stirrer.

The system was pressurized at room temperature with $CO_2$ up to 4.5 kg./sq.cm. The autoclave was then immersed in a thermostatic bath at 88° C. and the internal pressure raised up to 8 kg./sq.cm. with an internal temperature of 93° C. After a reaction time of 2.5 hours, the oxide was completely converted with a selectivity as mono-ethylene glycol (MEG) of 93%, as diethylene glycol of 5.8% and as ethylene carbonate of 0.2%.

EXAMPLE 2

25.3 g. of water, 8 g. of TEA and 7.1 g. of $CO_2$ were charged in the same apparatus described in the Example 1. 29.0 g. of ETO were then added. The system was immersed in a thermostatic bath at 94° C. and the pressure raised up to 18.5 kg./sq.cm., at a maximum internal temperature of 105° C. After a reaction time of 2.5 hours, the ETO was completely converted, with selectivities of 93.8% to MEG, 6% to DEG and 0.2% to ethylene carbonate.

EXAMPLE 3

25 g. of water, 8 g. of TEA and 8.5 g. of $CO_2$ were charged in the same apparatus of Example 1.

30 g. of ETO were then fed and the autoclave was immersed in a thermostatic bath at 100° C. The internal pressure increased up to 22 kg./sq.cm. and the internal temperature was 155° C.

After a reaction time of 2 hours, the ETO was completely converted, with selectivities of 93.2% to MEG, 6.7% to DEG and 0.1% to ethylene carbonate.

EXAMPLE 4

15 g. of water, 7.9 g. of TEA and 8.3 g. of $CO_2$ were charged in the same apparatus of Example 1.

29.7 g. of ETO were then added, and the autoclave was immersed in a thermostatic bath at 100° C.

The internal pressure increased up to 23.5 kg./sq.cm. and the temperature to 130° C.

After a reaction time of 3 hours, the ETO was completely converted with a selectivity of 92.9% to MEG, 7% to DEG and 0.1% to ethylene carbonate.

EXAMPLE 5

27.2 g. of $H_2O$, 29.3 g. of ETO and 5.8 g. of dimethylaniline were charged in the apparatus of Example 1.

At room temperature the autoclave was pressurized up to 4.5 kg./sq.cm. with $CO_2$ and then immersed in a thermostatic bath at 90° C. The internal pressure increased to 15 kg./sq.cm. and the temperature to 110° C.

After a reaction time of 2.5 hours, the total conversion of ETO was obtained with a selectivity of 91% to MEG, 8% to DEG and 1% to ethylene carbonate.

EXAMPLE 6

25 g. of $H_2O$, 29.5 g. of ETO, 5.8 g. of pyridine were charged in the same apparatus of Example 1. The pressure was increased to 4.5 kg./sq.cm. with $CO_2$ and the autoclave was immersed in a thermostatic bath at 90° C. The internal pressure increased up to 10 kg./sq.cm. and the temperature to 93° C.

After a reaction time of 4 hours, 80% of ETO was converted with a selectivity of 93.5% to MEG, 6% to DEG and 0.5% to ethylene carbonate.

EXAMPLE 7

371 g. of propylene oxide, 25 g. of water and 7.9 g. of TEA were charged in the same apparatus of Example 1.

The pressurization was carried out by 8 g. of $CO_2$ and the autoclave was immersed in a thermostatic bath at 105° C. The pressure was increased to 19 kg./sq.cm. and the temperature to 110° C.

After a reaction time of 2.5 hours, a conversion of 80% of the oxide was obtained with a selectivity of 97.5% to the mono-glycol, 2% to the di-glycols and 0.5% to propylene carbonate.

We claim:

1. A process for the preparation of alkylene glycols wherein the corresponding alkylene oxides are reacted with water and carbon dioxide in the presence of tertiary amines of the formula:

wherein $R_1$, $R_2$ and $R_3$ which are alike or different from each other, represent alkyl, aryl or cycloalkyl radicals, in an amount of between 0.1% and 20% by weight based on the feed.

2. A process for the preparation of alkylene glycols according to claim 1, characterized in that the reaction is carried out at a temperature of between 50° and 150° C.

3. A process for the preparation of alkylene glycols according to claim 1, characterized in that the reaction is carried out at a pressure of the carbon-dioxide of between 1 and 50 kg./sq.cm.

4. A process for the preparation of alkylene glycols according to claim 1 characterized in that the feed consists essentially of, the alkylene oxide, a tertiary amine, $CO_2$ and water.

5. A process for the preparation of ethylene glycol which comprises reacting ethylene oxide with water and carbon dioxide in the presence of from 0.1 to 20% by weight of triethylamine based on the weight of feed at a temperature between 50° and 150° C. and at a $CO_2$ pressure of between 1 and 50 kg./sq.cm.

6. A process for the preparation of ethylene glycol which comprises reacting ethylene oxide with water and carbon dioxide in the presence of from 0.1 to 20% by weight of triethylamine based on the weight of feed at a temperature between 50° and 150° C. and at a $CO_2$ pressure of between 1 and 50 kg./sq.cm.

7. A process for the preparation of ethylene glycol which comprises reacting ethylene oxide with water and carbon dioxide in the presence of from 0.1 to 20% by weight of pyridine based on the weight of feed at a temperature between 50° and 150° C. and at a $CO_2$ pressure of between 1 and 50 kg./sq.cm.

* * * * *

UNITED STATES PATENT AND TRADEMARK OFFICE
CERTIFICATE OF CORRECTION

PATENT NO. : 4,307,256

DATED : December 22, 1981

INVENTOR(S) : Gioacchino Cipriani, et al

It is certified that error appears in the above-identified patent and that said Letters Patent are hereby corrected as shown below:

Col. 4, line 16, change "triethylamine" to read

--dimethylaniline--.

Signed and Sealed this

Nineteenth Day of July 1983

[SEAL]

Attest:

Attesting Officer

GERALD J. MOSSINGHOFF

Commissioner of Patents and Trademarks